United States Patent [19]

Kawai et al.

[11] Patent Number: 4,808,567
[45] Date of Patent: Feb. 28, 1989

[54] DIVINYL COMPOUNDS AND CHROMOGENIC RECORDING-MATERIAL PREPARED BY USING THEREOF

[75] Inventors: Hajime Kawai; Yoshiharu Fujino, both of Tsuzuki; Youji Shimizu, Kyoto; Seiichi Nieda, Kyoto; Kazuhiko Gendai, Kyoto; Katsuhiko Tsunemitsu, Kyoto, all of Japan

[73] Assignee: Yamada Chemical Co., Ltd., Kyoto-fu, Japan

[21] Appl. No.: 37,669

[22] Filed: Apr. 13, 1987

[30] Foreign Application Priority Data

Apr. 15, 1986 [JP] Japan .................. 61-87619
Feb. 2, 1987 [JP] Japan .................. 62-23361

[51] Int. Cl.$^4$ ............... B41M 5/16; B41M 5/18; B41M 5/22; C07D 405/06
[52] U.S. Cl. .................. 503/220; 427/151; 548/523; 503/223; 546/96; 546/165; 546/166; 544/141; 540/602
[58] Field of Search .............. 548/463; 427/151; 503/220, 223

[56] References Cited

U.S. PATENT DOCUMENTS

| | | | |
|---|---|---|---|
| 4,020,056 | 4/1977 | Farber | 260/240 |
| 4,022,771 | 5/1977 | Farber | 260/240 D |
| 4,107,128 | 8/1978 | Farber | 542/437 |
| 4,119,776 | 10/1978 | Farber | 542/441 |
| 4,641,160 | 2/1987 | Kondo | 346/220 |

FOREIGN PATENT DOCUMENTS

| | | | |
|---|---|---|---|
| 0127203 | 3/1982 | European Pat. Off. | 548/463 |
| 0062544 | 4/1982 | European Pat. Off. | 548/463 |
| 0188377 | 1/1985 | European Pat. Off. | 548/463 |

Primary Examiner—Mary C. Lee
Assistant Examiner—J. Richter
Attorney, Agent, or Firm—Nixon & Vanderhye

[57] ABSTRACT

Disclosed herein are novel divinyl compounds represented by the formula (I):

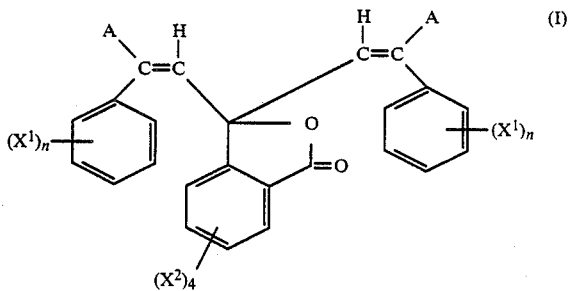

and a recording-material prepared by utilizing the divinyl compounds.

The present divinyl compound is in itself almost colorless, extremely stable in the atmosphere and develops rapidly blackish color by a developer. The color image given by the present divinyl compound is excellent in light-resistance and moisture-resistance and the letters developed can be read by an optical letter-reading apparatus or a barcord reading apparatus.

56 Claims, 3 Drawing Sheets

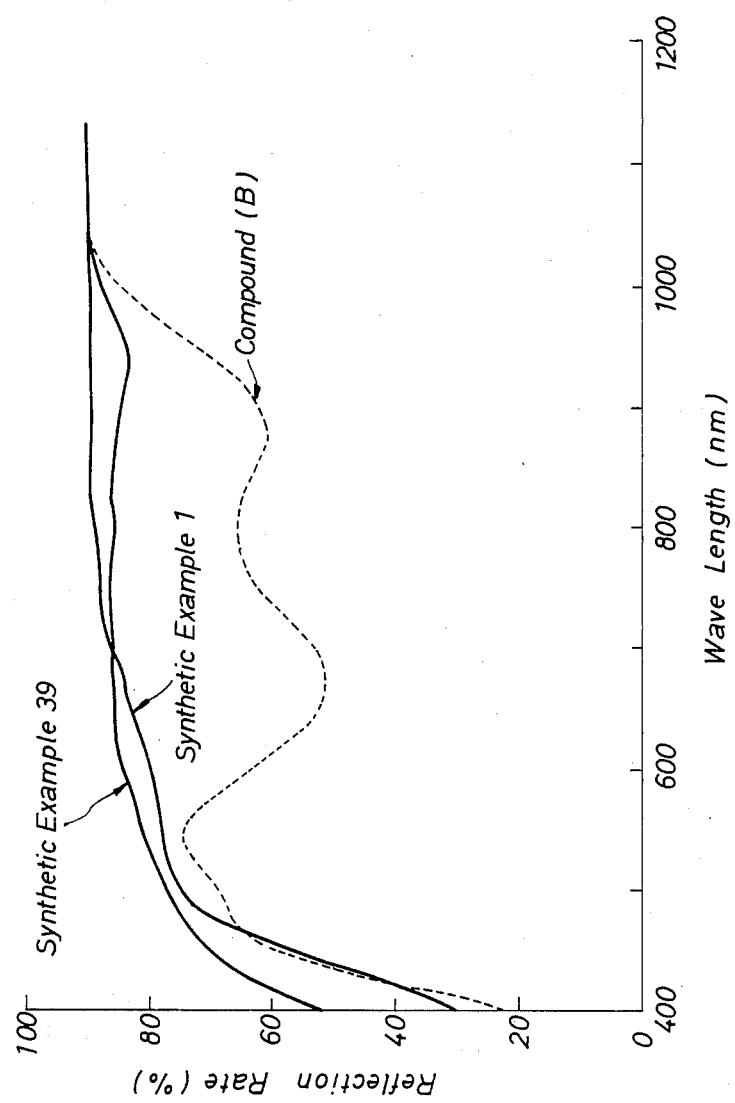

DIVINYL COMPOUNDS AND CHROMOGENIC RECORDING-MATERIAL PREPARED BY USING THEREOF

BACKGROUND OF THE INVENTION

The present invention relates to a recording-material such as pressure-sensitive recording paper, heat-sensitive recording paper, electro-heat sensitive recording paper, etc. More in detail, the present invention relates to a recording-material prepared by using a divinyl phthalide compound represented by the formula (I):

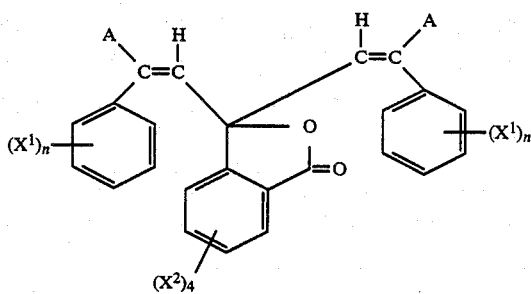

wherein A represents

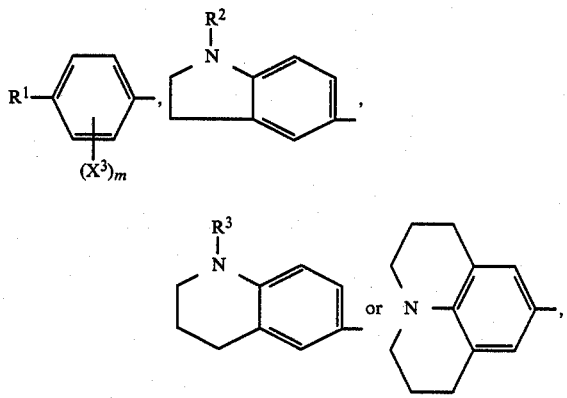

$X^1$ represents an alkyl group, an alkoxy group, an alkoxyalkoxy group, an aryloxy group, a cycloalkoxy group, a haloalkoxy group, an alkenyloxy group, an aralkyloxy group, a halogen atom or a combination thereof,
$X^2$ represents a halogen atom or a combination thereof,
$X^3$ represents an alkyl group of less than eight carbon atoms, an alkoxy group of less than eight carbon atoms, a halogen atom or a combination thereof,
$R^1$ represents a heterocyclic ring having one or more nitrogen atoms,
$R^2$ and $R^3$ represent respectively a hydrogen atom, an alkyl group, alkoxyalkyl group, a haloalkyl group or a combination thereof, and
m and n represent an integer of 0, 1, 2 or 3, respectively.

When m and n are not less than 2, $X^1$ of $(X^1)_n$, $X^2$ of $(X^2)_4$ and $X^3$ of $(X^3)_m$ can be same or different.

(Hereinafter the same sign means the same meaning.)

The divinyl phthalide compounds represented by the formula (I) are the novel compounds synthesized for the first time by the present inventors. The compounds are by themselvees almost colorless, extremely stable in the atmosphere, have no subliming property and spontaneously chromogenic property and dissolve extremely well in organic solvent. They give a blackish color rapidly by a developer and its color image is excellent in light-resistance and moisture-resistance. Furthermore, since the color image has a strong absorption between 700 and 1000 nm in addition of the visible region, the color image has a distinctive feature that it is possible to be read by the optical letter-reading apparatus using the near infrared rays (such as OCR and OMR) and the barcord reading apparatus. Namely, the divinyl phthalide compound of the present invention (hereinafter referred to as the present compound) is an extremely valuable and novel compound which can be used as a chromogenic agent for an ordinary recording-material developing black color, of which demand is rapidly increasing recently, as well as the material readable with OCR, OMR, etc.

The color image due to the black-coloring fluorane compound (A), which has been used as a conventional chromogenic agent for a recording-material, does not have any absorption in the near infrared region and accordingly, the color image could not be read by an optical letter-reading apparatus (refer to FIG. 2):

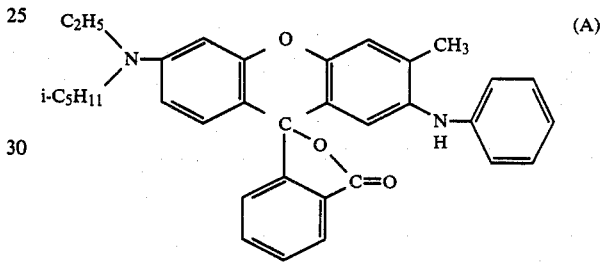

(refer to Japanese Patent Publication No. 56-52759/1981).

On the other hand, as the chromogenic agents having an absorption in the near infrared region, some compounds have been recently proposed in Japanese Patent Publication No. 58-5940/1983, Japanese Patent Application Laid-Open (KOKAI) No. 59-199757/1984 and Japanese Patent Application Laid-Open (KOKAI) No. 60-230890/1985. However, each of the proposed compounds has the following defects and any satisfactory chromogenic agent has not been obtained in the present situation.

Namely, the compound (B) of Japanese Patent Publication No. 58-5940/1983 and the compound (C) of Japanese Patent Application Laid-Open (KOKAI) No. 60-230890/1985 have been themselves strongly colored in yellow and besides, they are strong in the spontaneous coloring. These defects have very bad effect on production of the recording materials.

Although the fluorene compound (D) of Japanese Patent Application Laid-Open (KOKAI) No. 59-199757/1984 is colorless, the chromogenic property and the stability of color image are poor.

Furthermore, the hue of each of compounds (B), (C) and (D), when developed color, is green and accordingly, to obtain blackish color, another chromogenic agent giving red or black color must be added in a large amount, and since the chromogenic property and the chromogenic speed of each agent are different from those of compounds (B), (C) and (D) and particularly, the light-resistance of red-chromogenic agent is generally poor, bad influences such as unbalance of color-development and reduction of light-resistance could not be avoided.

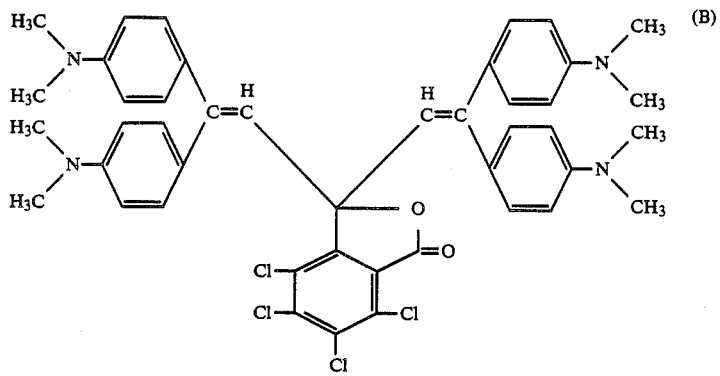

(refer to Japanese Patent Publication No. 58-5940/1983).

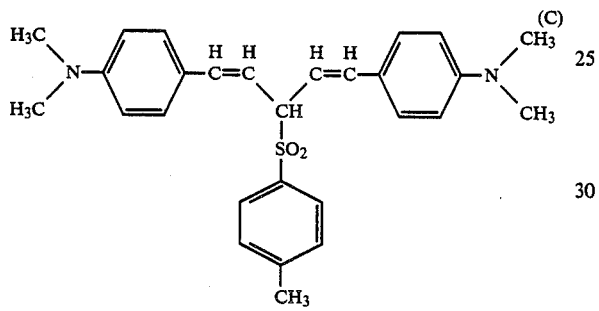

(refer to Japanese Patent Application Laid-Open (KOKAI) No. 60-230890/1985).

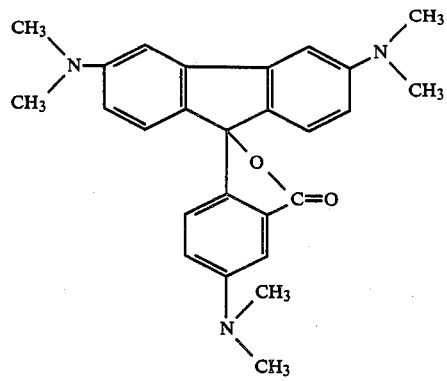

(refer to Japanese Patent Application Laid-Open (KOKAI) No. 59-199757/1984).

As a result of the present inventors' earnest studies to improve the defects of the conventional chromogenic agents, the present invention has been attained.

The present invention has been attained by the present inventors who have found out that the divinyl compounds (I) are unexpectedly excellent in several properties such as the solubility, the coloring of the compound itself, the hue of the developed color, the chromogenic property, the absorbancy of near infrared rays and the stability of color image and have studies further the problems, and the present invention provides the compounds represented by the formula (I) and a chromogenic recording materials, which contains the compound (I) as a chromogenic agent.

SUMMARY OF THE INVENTION

The object of the present invention lies in offering a novel divinyl compound represented by the following formula (I):

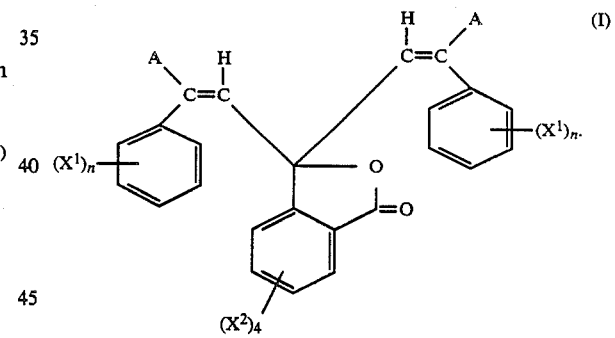

Furthermore, the object of the present invention lies in offering a chromogenic dye-precursor material of blackish color represented by the formula (I).

Still more, the object of the present invention lies in offering a recording-material characterized in that it contains the divinyl compound represented by the formula (I) as a chromogenic agent.

BRIEF EXPLANATION OF THE DRAWINGS

Of the attached drawings, FIG. 3 is the reflection spectra of a texture of heat-sensitive recording paper prepared with the present compound and the referenced compound.

DETAILED DESCRIPTION OF THE INVENTION

Figure 1:
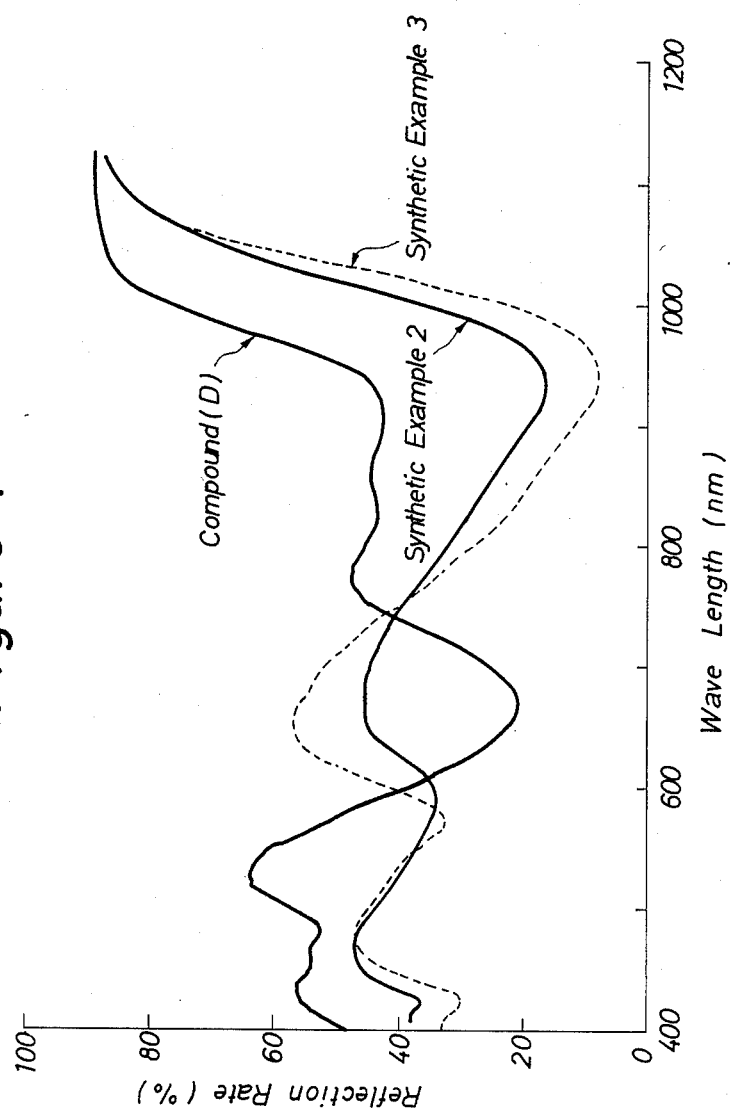
FIGS. 1 and 2 are the reflection spectra of a color images of pressure-sensitive and heat-sensitive recording papers, respectively, prepared with the present compound and the referenced compound

The present compound is a divinyl compound represented by the following formula (I):

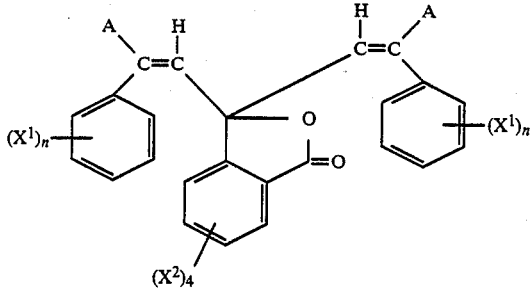

and as the concrete example thereof, the following compounds may be exemplified. Every compound is an almost colorless solid and develops a blue-black to black color rapidly by the action of activated clay.

1. 3,3-Bis[2-(p-pyrrolidinophenyl)-2-(p-methoxyphenyl)ethenyl]-4,5,6,7-tetrachlorophthalide,
2. 3,3-Bis[2-(p-pyrrolidinophenyl)-2-(p-ethoxyphenyl)ethenyl]-4,5,6,7-tetrachlorophthalide,
3. 3,3-Bis[2-(p-pyrrolidinophenyl)-2-(p-propoxyphenyl)ethenyl]-4,5,6,7-tetrachlorophthalide,
4. 3,3-Bis[2-(p-pyrrolidinophenyl)-2-(p-iso-propoxyphenyl)ethenyl]-4,5,6,7-tetrachlorophthalide,
5. 3,3-Bis[2-(p-pyrrolidinophenyl)-2-(p-butoxyphenyl)ethenyl]4,5,6,7-tetrachlorophthalide,
6. 3,3-Bis[2-(p-pyrrolidinophenyl)-2-(p-iso-butoxyphenyl)ethenyl]-4,5,6,7-tetrachlorophthalide,
7. 3,3-Bis[2-(p-pyrrolidinophenyl)-2-(p-sec-butoxyphenyl)ethenyl]4,5,6,7-tetrachlorophthalide,
8. 3,3-Bis[2-(p-pyrrolidinophenyl)-2-(p-tert-butoxyphenyl)ethenyl]4,5,6,7-tetrachlorophthalide,
9. 3,3-Bis[2-(p-pyrrolidinophenyl)-2-(m-methyl-p-methoxyphenyl)ethenyl]4,5,6,7-tetrachlorophthalide,
10. 3,3-Bis[2-(p-pyrrolidinophenyl)-2-(3,4-dimethoxyphenyl)ethenyl]-4,5,6,7-tetrachlorophthalide,
11. 3,3-Bis[2-(p-pyrrolidinophenyl)-2-phenyl-ethenyl]-4,5,6,7-tetrachlorophthalide,
12. 3,3-Bis[2-(p-pyrrolidinophenyl)-2-(p-methylphenyl)ethenyl]-4,5,6,7-tetrachlorophthalide,
13. 3,3-Bis[2-(p-pyrrolidinophenyl)-2-(p-methoxyphenyl)ethenyl]-4,5,6,7-tetrabromophthalide,
14. 3,3-Bis[2-(p-pyrrolidinophenyl)-2-(p-pentyloxyphenyl)ethenyl]-4,5,6,7-tetrachlorophthalide,
15. 3,3-Bis[2-(p-pyrrolidinophenyl)-2-(p-iso-pentyloxyphenyl)ethenyl]-4,5,6,7-tetrachlorophthalide,
16. 3,3-Bis[2-(p-pyrrolidinophenyl)-2-(p-chlorophenyl)ethenyl]-4,5,6,7-tetrachlorophthalide,
17. 3,3-Bis[2-(p-pyrrolidinophenyl)-2-(p-ethoxyphenyl)ethenyl]-4,5,6,7-tetrabromophthalide,
18. 3,3-Bis[2-(p-pyrrolidinophenyl)-2-(m-methoxy-p-ethoxyphenyl) ethenyl]-4,5,6,7-tetrachlorophthalide,
19. 3,3-Bis[2-(p-pyrrolidinophenyl)-2-(m-methyl-p-ethoxyphenyl)ethenyl]-4,5,6,7-tetrachlorophthalide,
20. 3,3-Bis[2-(p-pyrrolidinophenyl)-2-(p-methoxyphenyl)ethenyl]-5,6-dichloro-4,7-dibromophthalide,
21. 3,3-Bis[2-(p-pyrrolidinophenyl)-2-(p-methylphenyl)ethenyl]-5-chloro-4,6,7-tribromophthalide,
22. 3,3-Bis[2-(p-pyrrolidinophenyl)-2-(p-methylphenyl)ethenyl]-4,5,6,7-tetrabromophthalide,
23. 3,3-Bis[2-(p-pyrrolidinophenyl)-2-(o-methyl-p-methoxyphenyl)ethenyl]-4,5,6,7-tetrachlorophthalide,
24. 3,3-Bis[2-(p-pyrrolidinophenyl)-2-(3,4-dimethylphenyl)ethenyl]-4,5,6,7-tetrabromophthalide,
25. 3,3-Bis[2-(p-pyrrolidino-o-methylphenyl)-2-(p-methylphenyl)ethenyl]-4,5,6,7-tetrachlorophthalide,
26. 3,3-Bis[2-(p-pyrrolidinophenyl)-2-(p-ethylphenyl)ethenyl]-4,5,6,7-tetrachlorophthalide,
27. 3,3-Bis[2-(p-pyrrolidino-o-chlorophenyl)-2-(p-methoxyphenyl)ethenyl]-4,5,6,7-tetrachlorophthalide,
28. 3,3-Bis[2-(p-2,5-dimethylpyrrolidinophenyl)-2-(p-methylphenyl)ethenyl]-4,5,6,7-tetrachlorophthalide,
29. 3,3-Bis[2-(p-piperidinophenyl)-2-(p-methoxyphenyl)ethenyl]-4,5,6,7-tetrachlorophthalide,
30. 3,3-Bis[2-(p-piperidinophenyl)-2-(p-methylphenyl)ethenyl]-4,5,6,7-tetrachlorophthalide,
31. 3,3-Bis[2-(p-piperidinophenyl)-2-(p-methylphenyl)ethenyl]-4,5,6,7-tetrabromophthalide,
32. 3,3-Bis[2-(p-2-methylpiperidinophenyl)-2-phenyl-ethenyl]-4,5,6,7-tetrachlorophthalide,
33. 3,3-Bis[2-(p-4-methylpiperidinophenyl)-2-(p-methoxyphenyl)ethenyl]-4,5,6,7-tetrachlorophthalide,
34. 3,3-Bis[2-(p-hexamethyleneiminophenyl)-2-(p-methylphenyl)ethenyl]-4,5,6,7-tetrachlorophthalide.
35. 3,3-Bis[2-(p-morpholinophenyl)-2-(p-methoxyphenyl)ethenyl]-4,5,6,7-tetrachlorophthalide,
36. 3,3-Bis[2-(p-pyrrodinophenyl)-2-(p-octylphenyl)ethenyl]4,5,6,7-tetrachlorophthalide,
37. 3,3-Bis[2-(1-ethylindolin-5-yl)-2-(p-methylphenyl)ethenyl]-4,5,6,7-tetrachlorophthalide,
38. 3,3-Bis[2-(1-methylindolin-5-yl)-2-(p-methoxyphenyl)ethenyl]-4,5,6,7-tetrachlorophthalide,
39. 3,3-Bis[2-(1,2,3,4-tetrahydroquinolin-6-yl)-2-(p-methylphenyl)ethenyl]-4,5,6,7-tetrachlorophthalide,
40. 3,3-Bis[2-(1-methoxyethyl-1,2,3,4-tetrahydroquinolin-6-yl)-2-(p-methylphenyl)ethenyl]-4,5,6,7-tetrabromophthalide,
41. 3,3-Bis[2-durrolidinyl-2-(p-ethoxyphenyl)ethenyl]-4,5,6,7-tetrachlorophthalide,
42. 3,3-Bis[2-(p-pyrrolidinophenyl)-2-(p-methoxyethoxyphenyl)ethenyl]-4,5,6,7-tetrachlorophthalide,
43. 3,3-Bis[2-(p-pyrrolidinophenyl)-2-(p-allyloxyphenyl)ethenyl]-4,5,6,7-tetrachlorophthalide,
44. 3,3-Bis[2-(p-pyrrolidinophenyl)-2-(p-chloropropoxyphenyl)ethenyl]-4,5,6,7-tetrachlorophthalide,
45. 3,3-Bis[2-(p-pyrrolidinophenyl)-2-(p-cyclopentyloxyphenyl)ethenyl]-4,5,6,7-tetrachlorophthalide,
46. 3,3-Bis[2-(p-pyrrolidinophenyl)-2-(p-cyclohexyloxyphenyl)ethenyl]-4,5,6,7-tetrachlorophthalide,
47. 3,3-Bis[2-(p-pyrrolidinophenyl)-2-(p-benzyloxyphenyl)ethenyl]-4,5,6,7-tetrachlorophthalide,
48. 3,3-Bis[2-(p-pyrrolidinophenyl)-2-(p-phenoxyphenyl)ethenyl]-4,5,6,7-tetrachlorophthalide, and
49. 3,3-Bis{2-(p-pyrrolidinophenyl)-2-[p-(p-methoxyphenoxy)phenyl]ethenyl}-4,5,6,7-tetrachlorophthalide.

The divinylphthalide compounds according to the present invention can be synthesized by the method shown below.

As a first step, an ethylene derivative represented by the formula (2) is synthesized from a ketone by one of the following Grignard reactions a, b and c:

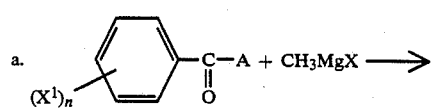

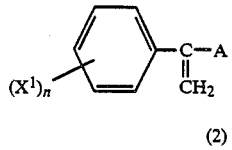

b. 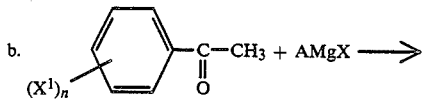

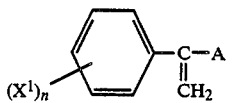

and c. 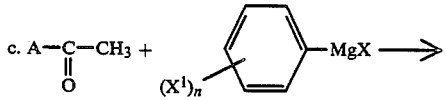

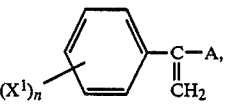

wherein X represents a halogen atom.

Then, 2 mols of the ethylene derivative (2) and 1 mol of a phthalic acid derivative (3) are condensated in the presence of a dehydrating agent such as acetic anhydride, sulfuric acid, etc., and by purifying the reaction product, the divinylphthalide compounds represented by the formula (I) are obtained as nearly colorless crystals.

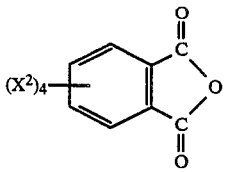

As the concrete examples of the ethylene derivatives represented by the formula (2), the following compounds can be exemplified:
1. 1-Phenyl-1-(p-pyrrolidinophenyl)ethylene,
2. 1-(p-methylphenyl)-1-(p-pyrrolidinophenyl)ethylene,
3. 1-(p-methoxyphenyl)-1-(p-pyrrolidinophenyl)ethylene,
4. 1-(p-ethoxyphenyl)-1-(p-pyrrolidinophenyl)ethylene,
5. 1-(p-butoxyphenyl)-1-(p-pyrrolidinophenyl)ethylene,
6. 1-(p-methoxyphenyl)-1-(p-pyrrolidino-o-methylphenyl)ethylene,
7. 1-(p-methoxyphenyl)-1-(p-pyrrolidino-o-methoxyphenyl)ethylene,
8. 1-(2,4-dimethylphenyl)-1-(p-pyrrolidinophenyl)ethylene,
9. 1-(2,4-dimethoxyphenyl)-1-(p-pyrrolidinophenyl)ethylene,
10. 1-(p-chlorophenyl)-1-(p-pyrrolidinophenyl)ethylene,
11. 1-(p-methylphenyl)-1-(p-2,5-dimethylpyrrolidinophenyl)ethylene,
12. 1-(p-methylphenyl)-1-(p-piperidinophenyl)ethylene,
13. 1-(p-methoxyphenyl)-1-(p-4-methylpiperidinophenyl)ethylene,
14. 1-(p-methylphenyl)-1-(p-hexamethyleneiminophenyl)ethylene,
15. 1-(p-methoxyphenyl)-1-(p-morpholinophenyl)ethylene,
16. 1-(p-methoxyphenyl)-1-(1-methylindoline-5-yl)ethylene,
17. 1-(p-methoxyphenyl)-1-(1-methyl-1,2,3,4-tetrahydroquinolin-6-yl)ethylene, and
18. 1-(p-methoxyphenyl)-1-durrolidinylethylene.

As phthalic acid derivatives represented by the formula (3), for instance, the following compounds can be mentioned.

Tetrachlorophthalic anhydride; 4-chloro-3,5,6-tribromophthalic anhydride; 4,5-dichloro-3,6-dibromophthalic anhydride; 4-bromo-3,5,6-trichlorophthalic anhydride; 4,5-dibromo-3,6-dichlorophthalic anhydride; tetrabromophthalic anhydride; tetrafluorophthalic anhydride; tetraiodophthalic anhydride; 4,5-dichloro-3,6-difluorophthalic anhydride; 4-chloro-3,5,6-triiodophthalic anhydride and 4,5-dichloro3,6-diiodophthalic anhydride.

In case where a pressure-sensitive recording paper, a heat-sensitive recording paper, etc. is produced with these divinylphthalide compounds, one or more of the compounds can be used. By mixing not less than two of the compounds, the chromogenic property and the stability in preserving the color image are improved. Moreover, to make the hue and the concentration of developed color, and the stability of color image more complete, various known chromogenic agents which give various hues can be used with the present compound to the extent not to damage the facilities of the present compound.

For instance, the present compound can be used with the chromogenic agent which has the fundamental skeleton such as 3,3-bis(aminophenyl)-6-aminophthalide, 3,3-bis(indolyl)phthalide, 3-aminofluoran, aminobenzofluoran, 2,6-diaminofluoran, 2,6-diamino-3-methylfluoran, spiropyrane, phenothiazine, phenoxazine, leucoauramine, diarylcarbazolylmethane, 3-indolyl-3-(aminophenyl)azaphthalide, triaminofluorenephthalide, tetraaminodivinylphthalide.

When producing a pressure-sensitive recording paper, as a solvent for a chromogenic agent, various solvents of alkylbenzene series, alkylbiphenyl series, alkylnaphthalene series, diarylethane series, hydrogenated terphenyl series and chlorinated paraffin series can be used singly or as a mixture, and for encapsulation, a coacervation method, an interfacial polymerization method or an In-situ method can be applied.

As a developer, clays such as bentonite, activated clay, acid clay, etc.; metal salt of salicylic acid, salicylic ester derivatives, salicylic acid derivatives, etc.; hydroxy compounds such as 2,2-bis(p-hydroxyphenyl)propane (bisphenol A), esters of p-hydroxybenzoic acid, etc.; p-phenylphenol-formaldehyde resin, p-octylphenolformaldehyde resin and metal salt thereof, are used.

When producing a heat-sensitive recording paper, as a binder, polyvinyl alcohol, methylcellulose, hydroxyethylcellulose, carboxymethylcellulose, gum arabic, gelatine, caseine, starch, polyvinyl pyrrolidone, copolymer of styrene and maleic anhydride, can be used.

As a developer, one or more of the following hydroxy compounds can be used: p-phenylphenol, p-hydroxydiphenyl ether, methyl p-hydroxybenzoate, benzyl p-hydroxybenzoate, 2,2-bis(p-hydroxyphenyl)-propane, 4,4'-thiodiphenol, bis-(4-hydroxy-3-methylphenyl) sulfide, 4,4'-dihydroxydiphenylsulfone, 4-hydroxy-4'-methyldiphenylsulfone, 4-hydroxy-4'-ethyldiphenylsulfone, 3,4-dihydroxy-4'-methyldiphenylsulfone, 4-hydroxy-4'-isopropoxydiphenylsulfone, 4,4'-dihydroxy-3,3'-dimethyldiphenylsulfone, 4,4'-dihydroxy-3,3'-diallyldiphenylsulfone, 1,5-di(4-hydroxyphenylthio)-3-oxapentane, 1,7-di(4-hydroxy-phenylthio)-3,5-dioxaheptane, 1,8-di(4-hydroxyphenylthio)-3,6-dioxaoctane, bis(4-hydroxy-3-methylphenyl) sulfide, etc.

As a sensitivity-improving agent, acetoanilide; paraffin wax; carnauba wax; higher fatty acids; esters of a higher fatty acid; amides of a higher fatty acid; phthalic esters; terephthalic esters; benzyl 4-benzyloxybenzoate; naphthol benzyl ether; 1,4-dialkoxynaphthalene; m-terphenyl; p-benzylbiphenyl, dibenzylbenzene; esters of 1-hydroxy-2-naphthoic acid; 1-phenoxy-2-naphthoxy-1-ethane; 1,2-di(3-methylphenoxy)ethane; 1-(2-isopropylphenoxy)-2-naphthoxy2-ethane; esters of 2-hydroxy-3-naphthoic acid; 4,4'-dialkoxydiphenylsulfone; benzamide; diphenylamine, benzenesulfonamide; benzenesulfonanilide; carbazole, hydroquinone dibenzyl ether; diphenyl carbonate, etc. can be used singly or after mixing together.

Furthermore, in order to improve the lightresistance and the preservability of the color image, it is effective to add an anti-oxidant, an anti-deteriorant or an ultraviolet absorbent, or to overcoat a high polymeric substance.

The present invention will be concretely explained while referring to the Synthetic Examples of the compound represented by the formula (I) and the Production Examples of the chromogenic recording-material with the compound represented by the formula (I) as follow.

SYNTHETIC EXAMPLE 1

Synthesis of 3,3-bis[2-(p-pyrrolidinophenyl)-2-(p-methoxyphenyl)ethenyl]-4,5,6,7-tetrachlorophthalide.

Into a mixture of 25 ml of acetic anhydride and 75 ml of o-dichlorobenzene, 14.0 g of 1-(p-methoxyphenyl)-1-(p-pyrrolidinophenyl)ethylene (m.p. 115°–118° C.) and 21.5 g of tetrachlorophthalic anhydride were added and the mixture was stirred for 6 hours at 120° C. Into 200 ml of water the reaction mixture was added and after making the mixture alkaline by adding sodium hydroxide, the alkaline reaction mixture was extracted with 70 ml of toluene. The solid matter obtained by evaporating toluene from the extract was recrystallized from acetone while purifying with activated carbon to obtain 17.6 g of pale yellow crystals melting at 159° to 161° C. (Yield: 85.2%)

From the elementary analysis, the infrared absorption spectrum and the nuclear magnetic resonance spectrum of the product obtained, it was confirmed that the product was represented by the following formula:

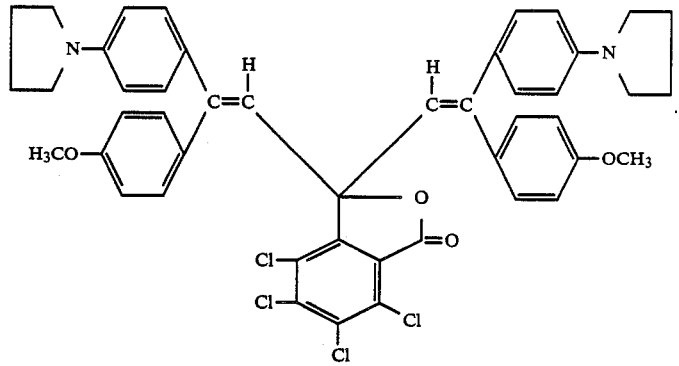

The compound was colored rapidly into blue-black by activated clay and the $\lambda_{max}$ thereof in methanol.stannic chloride was 900 nm.

The ethylene derivative, 1-(p-methoxyphenyl)-1-(p-pyrrolidinophenyl)ethylene, used in the above reaction, was synthesized as follows.

Into 30 ml of ether, 4 g of metallic magnesium were added and then 0.2 ml of methyl iodide was added to the mixture. After stirring the mixture for a while, a solution prepared by dissolving 24.8 g of methyl iodide into 40 ml of ether was added to the mixture taking 2 hours under a reflux condenser while stirring the mixture.

Separately, a solution was prepared by mixing 19.7 g of 4-methoxy-4'-pyrrolidinobenzophenone (melting at 152°–154° C.) and 100 ml of tetrahydrofurane, and the solution was slowly added to the liquid reaction mixture and the whole matter was stirred for one hour at a temperature of 40 to 50° C. Then the whole matter was mixed with 400 ml of water and 300 ml of toluene and after making the mixture weakly acidic by dilute hydrochloric acid, the acidified mixture was stirred for a while at 80° C. and separated into an aqueous layer and an organic layer (toluene layer). After adding activated carbon to the toluene layer and filtering the layer while hot, toluene was distilled off from the filtrate to obtain 18.5 g of 1-(p-methylxyphenyl)-1-(p-pyrrolidinophenyl)ethylene of pale yellow in color.

SYNTHETIC EXAMPLE 2

Synthesis of 3,3-bis[2-(p-pyrrolidinophenyl)-2-(p-ethoxyphenyl)ethenyl]-4,5,6,7-tetrachlorophthalide.

Into 50 ml of acetic anhydride 14.7 g gf 1-(p-ethoxyphenyl)-1-(p-pyrrolidinophenyl)ethylene (m.p. 134°–136° C.) and 14.3 g of tetrachlorophthalic anhydride were added and the mixture was stirred for 6 hours at 115° C. Into 200 ml of water the reaction mixture was added and after making the mixture alkaline by adding sodium hydroxide, the alkaline reaction mixture was extracted with 70 ml of toluene. The solid matter obtained by evaporating toluene from the extract was recrystallized from acetone while purifying with activated carbon to obtain 17.7 g of pale yellow crystals melting at 221° to 223° C. (Yield: 82.9%).

From the elementary analysis, the infrared absorption spectrum and the nuclear magnetic resonance spectrum of the product obtained, it was confirmed that the product was represented by the following formula:

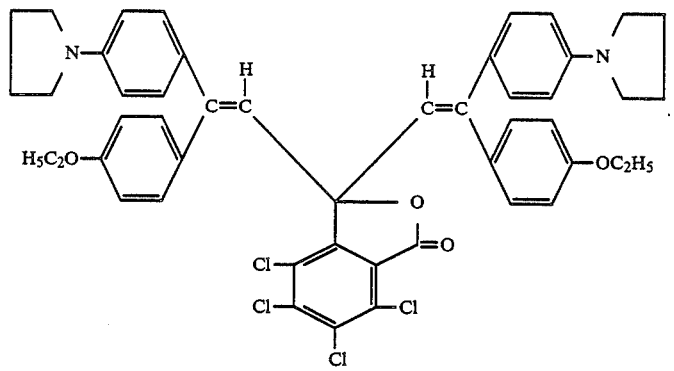

The compound was colored rapidly into blue-black by activated clay and the $\lambda_{max}$ thereof in methanol.stannic chloride was 897 nm.

SYNTHETIC EXAMPLE 3

Synthesis of 3,3-bis{2-(p-pyrrolidinophenyl)-2-[p-(p-methoxyphenoxy)phenyl]ethenyl}-4,5,6,7-tetrachlorophthalide.

Into a mixture of 10 ml of acetic anhydride and 25 ml of o-dichlorobenzene, 14.3 g of tetrachlorophthalic anhydride was added and then 18.6 g of 1-[p-(p-methoxyphenoxy)phenyl]-1-(p-pyrrolidinophenyl)ethylene (m.p. 123.5°–124.5° C.) was added dropwise for 1 hour at 120° C. and the mixture was stirred for 2 hours at the same temperature. Into 200 ml of water the reaction mixture was added and after making the mixture alkaline by adding sodium hydroxide, the alkaline reaction mixture was extracted with 70 ml of toluene. The solid matter obtained by evaporating toluene from the extract was recrystallized from ethyl alcohol while purifying with activated carbon and obtained 18.2 g of pale yellow crystals melting at 95° C. (decomposed).

From the elementary analysis, the infrared absorption spectrum and the nuclear magnetic resonance spectrum of the product obtained, it was confirmed that the product was represented by the following formula:

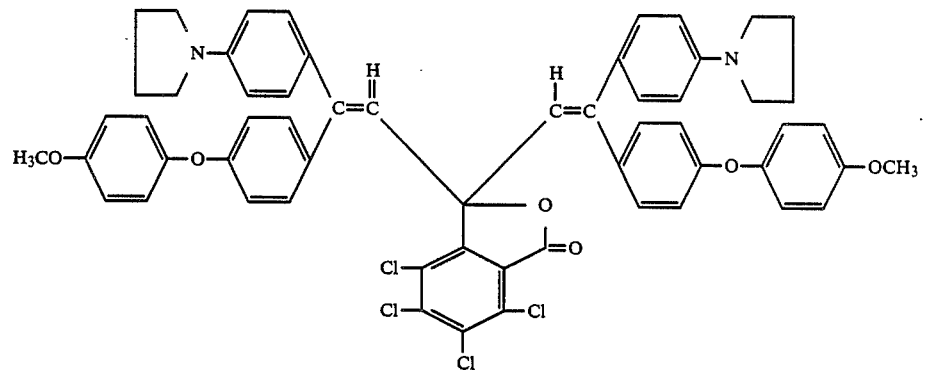

The compound was colored rapidly into blue-black by activated clay and the $\lambda_{max}$ thereof in methanol. stannic chloride was 910 nm.

SYNTHETIC EXAMPLES 4 to 43

By bringing various ethylene derivatives into reaction with various phthalic acid derivatives in the same manner as in Synthetic Examples 1, 2 and 3, the divinyl compounds shown in Table 1 were synthesized. All the compounds were solid and colorless to pale yellow in color. They were colored rapidly into the hue shown in Table 1.

For preparing a pressure-sensitive recording paper with the divinyl compound represented by the formula (I), any publicly known method can be used, for instance, the coacervation method disclosed in U.S. Pat. Nos. 2,800,458 and 2,806,457. For preparing the heat-sensitive recording paper, a publicly known method, for instance, the method disclosed in Japanese Patent Publication No. 45-14039/1960, can be used.

TABLE 1

| Compound Number | A | $X^1$ | $X^2$ | Color | $\lambda_{max}$ (nm) | M. P. (°C.) |
|---|---|---|---|---|---|---|
| 4 | ⟨pyrrolidino-phenyl⟩ | p-n-$C_3H_7O-$ | Cl | Blue black | 898 | 208–210 |

TABLE 1-continued

| Compound Number | A | X¹ | X² | Color | $\lambda_{max}$ (nm) | M.P. (°C.) |
|---|---|---|---|---|---|---|
| 5 | " | p-iso-$C_3H_7O-$ | Cl | Blue black | 900 | 205–208 |
| 6 | " | p-n-$C_4H_9O-$ | Cl | Blue black | 900 | 168–171 |
| 7 | " | p-i-$C_4H_9O-$ | Cl | Blue black | 902 | 192–194 |
| 8 | " | p-s-$C_4H_9O-$ | Cl | Blue black | 900 | 157–160 |
| 9 | pyrrolidinyl-phenyl | p-t-$C_4H_9O-$ | Cl | Blue black | 900 | 149–152 |
| 10 | " | n-$CH_3O-$, m-$CH_3-$ | Cl | Blue black | 898 | 165–167 |
| 11 | " | 3,4-$(CH_3O)_2-$ | Cl | Blue black | 910 | 190–192 |
| 12 | " | — (n = 0) | Cl | Black | 920 | 218–221 |
| 13 | " | p-$CH_3-$ | Cl | Black | 910 | 152~154 |
| 14 | " | p-$CH_3O-$ | Br | Blue black | 904 | 162~165 |
| 15 | " | n-$C_5H_{11}O-$ | Cl | Blue black | 900 | 136–139 |
| 16 | pyrrolidinyl-phenyl | p-i-$C_5H_{11}O-$ | Cl | Blue black | 902 | 118~122 |
| 17 | " | p-Cl— | Cl | Black | 930 | 95~100 |
| 18 | " | p-$C_2H_5O-$ | Br | Blue black | 902 | 217–219 |
| 19 | " | p-$C_2H_5O-$, | Cl | Blue black | 910 | 145~148 |
| 20 | " | p-$C_2H_5O-$, m-$CH_3-$ | Cl | Blue black | 900 | 170–173 |
| 21 | " | p-$CH_3O-$ | 5,6-$Cl_2-$, 4,7-$Br_2-$ | Blue black | 902 | 164–166 |
| 22 | " | p-$CH_3OC_2H_4O-$ | Cl | Blue black | 905 | Difficult to crystallize |
| 23 | pyrrolidinyl-phenyl | p-cyclohexyl-O— | Cl | Blue black | 902 | 135–138 |
| 24 | " | p-$C_6H_4$-$CH_2O-$ | Cl | Blue black | 903 | 151–155 |
| 25 | " | p-$CH_3O$-$C_6H_4$-O— | Br | Blue black | 910 | Difficult to crystallize |
| 26 | " | p-$CH_3O-$ | 5-Cl—, $Br_3-$ | Black | 900 | 135–138 |
| 27 | " | 3,4-$(CH_3)_2-$ | Cl | Black | 910 | 168~170 |
| 28 | pyrrolidinyl-(3-OCH₃)-phenyl | p-$CH_3O-$ | Cl | Black | 840 | Difficult to crystallize |
| 29 | pyrrolidinyl-(3-OC₂H₅)-phenyl | p-$CH_3-$ | Cl | Black | 850 | Difficult to crystallize |

TABLE 1-continued

| Compound Number | A | X¹ | X² | Color | $\lambda_{max}$ (nm) | M. P. (°C.) |
|---|---|---|---|---|---|---|
| 30 | 2,6-dimethylpiperidinyl-N-phenyl | p-CH₃— | Cl | Black | 910 | 128–131 |
| 31 | piperidinyl-N-phenyl | p-C₂H₅O— | Cl | Blue black | 890 | 180~185 |
| 32 | 4-methylpiperidinyl-N-phenyl | p-CH₃— | 5,6-Cl₂—, 4,5-Br₂— | Black | 910 | Difficult to crystallize |
| 33 | piperidinyl-N-phenyl | p-OCH₃— | Cl | Blue black | 905 | 180–184 |
| 34 | morpholinyl-N-phenyl | — (n = 0) | Cl₄ | Black | 910 | Difficult to crystallize |
| 35 | 1-methylindolinyl | p-CH₃O— | Cl | Black | 910 | Difficult to crystallize |
| 36 | 1-methyl-1,2,3,4-tetrahydroquinolinyl | p-CH₃O— | Br | Black | 922 | 163–166 |
| 37 | 1-methyl-1,2,3,4-tetrahydroquinolinyl | p-CH₃O— | 5-Cl—, Br₃— | Black | 923 | Difficult to crystallize |
| 38 | 1-methyl-1,2,3,4-tetrahydroquinolinyl | p-CH₃O— | 5,6-Cl₂—, Br₂— | Black | 921 | 145–148 |
| 39 | '' | p-CH₃O— | Cl | Black | 915 | 150° C. (decomposition) |
| 40 | pyrrolidinyl-N-phenyl | p-n-C₃H₇O—, m-CH₃— | Cl | Blue black | 900 | 132–135 |
| 41 | '' | p-iso-C₃H₇O—, m-CH₃— | Cl | Blue black | 898 | 148–151 |
| 42 | '' | 3,4-(C₂H₅O)₂— | Cl | Blue black | 910 | 165–168 |
| 43 | '' | p-C₈H₁₇O— | Cl | Blue black | 900 | Difficult to crystallize |

PRODUCTION EXAMPLE 1

Production of a pressure-sensitive copying paper.

Into 95 parts by weight of monoisopropylbiphenyl, 5 parts by weight of the compound of Example 2, namely, 3,3-bis[2-(p-pyrrolidinophenyl)-2-(p-ethoxyphenyl)ethenyl]-4,5,6,7-tetrachlorophthalide, were dissolved and a solution of 24 parts by weight of gelatine and 24 parts by weight of gum arabic into 400 parts by weight of water, of which pH was adjusted to 7, was added to the monoisopropylbiphenyl solution and the mixture was emulsified by a homogenizer. Into the emulsion, 100 parts by weight of warm water were added and after stirring the mixture for 30 minutes at 50° C. about one part by weight of an aqueous 10% solution of sodium hydroxide was added and the mixture was further stirred for another 30 minutes at the same temperature.

In the next step, dilute acetic acid was added to the mixture to adjust the pH to 4.5 and after stirring for about one hour at 50° C., the mixture was cooled to 0° to 5° C. and stirred for 30 minutes. Then, 35 parts by weight of an aqueous 4% solution of glutaraldehyde were slowly added to the mixture to harden the resulting capsules and pH of the mixture was adjusted to 6 by adding a dilute aqueous solution of sodium hydroxide to complete the capsulation. During the operations, no coloring was observed.

The capsule suspension obtained was uniformly coated on a sheet of paper by a wire-bar so that the coated weight of capsules after drying became 6 g/m² and the sheet was dried to obtain a capsule-coated paper sheet (the upper paper sheet).

On piling the upper paper sheet onto a sheet of paper coated with a phenol-formaldehyde resin as a developer and applying writing pressure by a ball-pen on the sheets of paper, letters of deep black in color rapidly appeared on the piled-up sheets of paper.

The color image appeared were excellent in light-resistance and moisture-resistance and since the image had a strong absorption in the range of 800 to 1000 nm, it was possible to read the letters by OCR. Furthermore, the surface of the paper coated with the capsules had an excellent light-resistance, and its color and chromogenic ability were not reduced by sun light.

COMPARATIVE EXAMPLE 1

In the same manner as in Production Example 1 except for using 5 parts by weight of the compound (D) as the chromogenic agent, a pressure-sensitive copying paper was prepared.

On subjecting the pressure-sensitive copying paper to color-development by a lower paper sheet on which a phenolformaldehyde resin had been applied, a light green image appeared slowly.

As the absorption of near infrared rays by the image was weak, it was difficult to read it by OCR (refer to FIG. 1).

PRODUCTION EXAMPLE 2

Production of a heat-sensitive recording paper:
(1) Preparation of a liquid dispersion of a chromogenic agent (A-liquid):

A mixture of the following recipe was pulverized by a paintshaker (made by TOYO-SEIKI Co., Ltd.) until the mean diameter of the particles of the chromogenic agent became 2 μm:

5 parts by weight of 3,3-bis[2-(p-pyrrodinophenyl)-2-(p-methoxyphenyl)ethenyl]-4,5,6,7tetrachlorophthalide (Synthetic Example 1), 15 parts by weight of kaoline, 100 parts by weight of an aqueous 10% solution of polyvinyl alcohol and 85 parts by weight of water.

(2) Preparation of a liquid dispersion of a developer and a sensitizer (B-liquid):

A mixture of the following recipe was pulverized by a paintshaker until the mean diameter of the particles of developer and sensitizer became 3 μm:

15 parts by weight of bisphenol A, 10 parts by weight of zinc stearate, 15 parts by weight of stearic amide and 150 parts by weight of an aqueous 10% solution of polyvinyl alcohol.

(3) Preparation and application of a liquid heat-sensitive material:

By mixing 10 parts by weight of A-liquid and 6.5 parts by weight of B-liquid, a liquid heat-sensitive material was obtained. The liquid material was coated on a sheet of paper by a wire-bar uniformly so that the coated weight of solid materials after drying became 6 g/m² and the sheet of paper was dried to obtain a heat-sensitive recording paper.

The heat-sensitive recording paper was nearly colorless and did not show any spontaneous coloring (refer to FIG. 3). The heat-sensitive recording paper showed a dark-black color by the heating with a heated pen. The color image obtained was excellent in light-resistance and moisture-resistance and as the color image had a strong absorption in the range of 700 and 1050 nm, it was possible to read the image by OCR.

The same results have been obtained on using the compounds in another Synthetic Examples.

COMPARATIVE EXAMPLE 2

Figure 2:
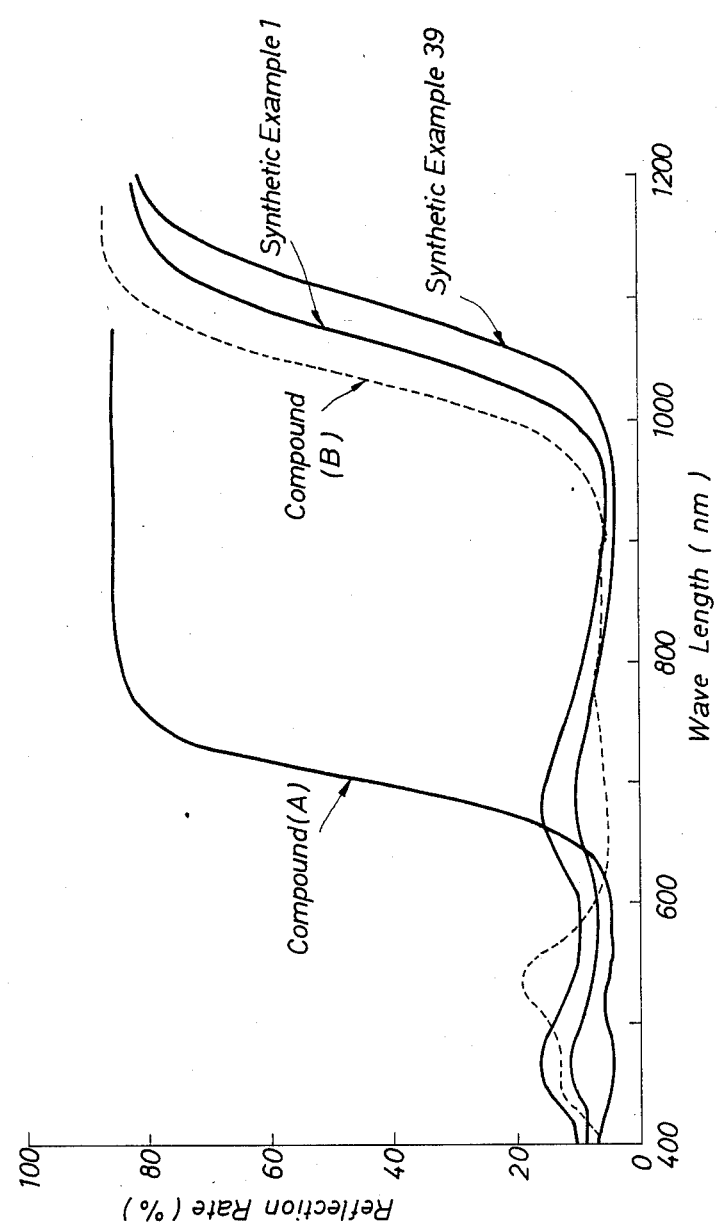

In the same manner as in Production Example 2 except for using 5 parts by weight of the compound (A), a heat-sensitive recording paper was obtained. Although the heat-sensitive recording paper was colored into black by heating with a heated pen, as the color image did not absorb any near infrared rays, it was impossible to read the color image by OCR (refer to FIG. 2).

COMPARATIVE EXAMPLE 3

In the same manner as in Production Example 2 except for using 5 parts by weight of the compound (B), a heat-sensitive recording paper was obtained. The heat-sensitive recording paper showed yellowish green spontaneous coloring. On heating the paper with a heated pen, green color was developed (refer to FIGS. 2 and 3).

From the above Production Examples and Comparative Examples, it has been confirmed that the divinyl compound according to the present invention is the excellent chromogenic agent for the recording materials.

What is claimed is:

1. A divinyl compound represented by the formula (I):

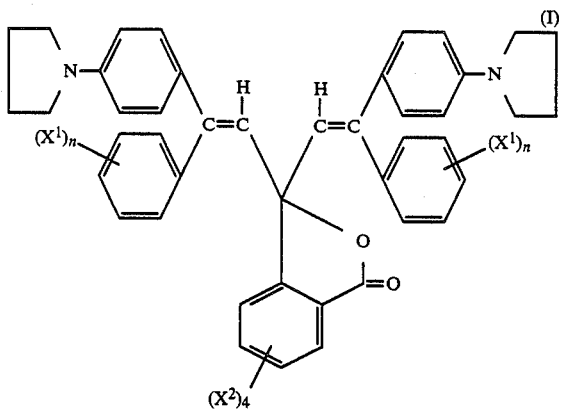

wherein $X^1$ is selected from the group consisting of an alkyl group of not more than six carbon atoms, an alkoxy group of not more than eight carbon atoms, an alkoxy-alkoxy group of not more than six carbon atoms in total, a phenoxy group, a cycloalkoxy group of not more than eight carbon atoms, a haloalkoxy group of not more than eight carbon atoms, an alkenyloxy group of not more than eight carbon atoms, a benzyloxy group and a halogen atom; $X^2$ represents a halogen atom; and n represents an integer of 0, 1, 2 or 3, wherein $X^1$ of $(X^1)_n$ can be the same or different when n is not less than 2 and $X^2$ of $(X^2)_4$ can be the same or different.

2. A divinyl compound according to claim 1, wherein $X^1$ is selected from an alkyl group of not more than six carbon atoms, an alkoxy group of not more than six carbon atoms, a cyclohexyloxy group, a cyclopentyloxy group, a benzlyloxy group, an allykoxy group, an alkoxyalkoxy group of not more than 6 carbon atoms in total, a phenoxy group, a phenoxy group substituted by an alkyl group of not more than eight carbon atoms or an alkoxy group of not more than eight carbon atoms, and a halogen atom; $(X^2)_4$ represents four chlorine atoms, four bromine atoms, one chlorine atom and three bromine atoms or two chlorine atoms and two bromine atoms; and n is 0, 1 or 2.

3. A divinyl compound according to claim 1, wherein n is 1.

4. A divinyl compound according to claim 1, wherein $X^1$ is an alkoxy group of not more than four carbon atoms in a para-position and n is 1.

5. A divinyl compound according to claim 1, wherein said divinyl compound is 3,3-bis[2-(p-pyrrolidino-phenyl)-2-(p-methoxyphenyl)ethenyl]-4,5,6,7-tetrachlorophthalide.

6. A divinyl compound according to claim 1, wherein said divinyl compound is 3,3-bis[2-(p-pyrrolidino-phenyl)-2-(p-ethoxyphenyl)ethenyl]-4,5,6,7-tetrachlorophthalide.

7. A divinyl compound according to claim 1, wherein said divinyl compound is 3,3-bis[2-(p-pyrrolidino-phenyl)-2-(p-propoxyphenyl)ethenyl]-4,5,6,7-tetrachlorophthalide.

8. A divinyl compound according to claim 1, wherein said divinyl compound is 3,3-bis[2-(p-pyrrolidino-phenyl)-2-(p-isopropoxyphenyl)ethenyl]-4,5,6,7-tetrachlorophthalide.

9. A divinyl compound according to claim 1, wherein said divinyl compound is 3,3-bis[2-(p-pyrrolidino-phenyl)-2-(p-butoxyphenyl)ethenyl]-4,5,6,7-tetrachlorophthalide.

10. A divinyl compound according to claim 1, wherein said divinyl compound is 3,3-bis[2-(p-pyrrolidino-phenyl)-2-(p-isobutoxyphenyl)ethenyl]-4,5,6,7-tetrachlorophthalide.

11. A divinyl compound according to claim 1, wherein said divinyl compound is 3,3-bis[2-(p-pyrrolidinophenyl)-2-(p-sec-butoxyphenyl)ethenyl]-4,5,6,7-tetrachlorophthalide.

12. A divinyl compound according to claim 1, wherein said divinyl compound is 3,3-bis[2-(p-pyrrolidino-phenyl)-2-(p-tert-butoxyphenyl)ethenyl]-4,5,6,7-tetrachlorophthalide.

13. A divinyl compound according to claim 1, wherein said divinyl compound is 3,3-bis[2-(p-pyrrolidinophenyl)-2-(m-methyl-p-methoxyphenyl)ethenyl]-4,5,6,7-tetrachlorophthalide.

14. A divinyl compound according to claim 1, wherein said divinyl compound is 3,3-bis[2-(p-pyrrolidinophenyl)-2-(3,4-dimethoxyphenyl)ethenyl]-4,5,6,7-tetra-chlorophthalide.

15. A divinyl compound according to claim 1, wherein said divinyl compound is 3,3-bis[2-(p-pyrrolidinophenyl)-2-phenylethenyl]-4,5,6,7-tetra-chlorophthalide.

16. A divinyl compound according to claim 1, wherein said divinyl compound is 3,3-bis[2-(p-pyrrolidino-phenyl)-2-(p-methylphenyl)ethenyl]-4,5,6,7-tetrachlorophthalide.

17. A divinyl compound according to claim 1, wherein said divinyl compound is 3,3-bis[2-(p-pyrrolidinophenyl)-2 -(p-methoxyphenyl)ethenyl]-4,5,6,7-tetrabromophthalide.

18. A divinyl compound according to claim 1, wherein said divinyl compound is 3,3-bis[2-(p-pyrrolidino-phenyl)-2-(pentyloxyphenyl)ethenyl]-4,5,6,7-tetrachlorophthalide.

19. A divinyl compound according to claim 1, wherein said divinyl compound is 3,3-bis[2-(p-pyrrolidinophenyl)-2-(p-isopentyloxyphenyl)ethenyl]-4,5,6,7-tetrachlorophthalide.

20. A divinyl compound according to claim 1, wherein said divinyl compound is 3,3-bis[2-(p-pyrrolidinophenyl)-2-(p-chlorophenyl)ethenyl]-4,5,6,7-tetrachlorophthalide.

21. A divinyl compound according to claim 1, wherein said divinyl compound is 3,3-bis[2-(p-pyrrolidinophenyl)-2-(p-ethoxyphenyl)ethenyl]-4,5,6,7-tetrabromophthalide.

22. A divinyl compound according to claim 1, wherein said divinyl compound is 3,3-bis[2-(p-pyrrolidinophenyl)-2-(m-methoxy-p-ethoxyphenyl)ethenyl]-4,5,6,7-tetrachlorophthalide.

23. A divinyl compound according to claim 1, wherein said divinyl compound is 3,3-bis[2-(p-pyrrolidinophenyl)-2-(m-methyl-p-ethoxyphenyl)ethenyl]-4,5,6,7-tetrachlorophthalide.

24. A divinyl compound according to claim 1, wherein said divinyl compound is 3,3-bis[2-(p-pyrrolidinophenyl)-2-(p-methoxyphenyl)ethenyl]-5,6-dichloro-4,7-dibromophthalide.

25. A divinyl compound according to claim 1, wherein said divinyl compound is 3,3-bis{2-(p-pyrrolidinophenyl-2-[p-(p-methoxyphenoxy)phenyl]ethenyl}-4,5,6,7-tetrachlorophthalide.

26. A divinyl compound according to claim 1, wherein said divinyl compound is 3,3-bis[2-(p-pyrrolidinophenyl)-2-(m-methyl-p-n-propoxyphenyl)ethenyl]-4,5,6,7-tetrachlorophthalide.

27. A divinyl compound according to claim 1, wherein said divinyl compound is 3,3-bis[2-(p-pyrrolidinophenyl)-2-(m-methyl-p-iso-propoxyphenyl)ethenyl]-4,5,6,7-tetrachlorophthalide.

28. A divinyl compound according to claim 1, wherein said divinyl compound is 3,3-bis[2-(p-pyrrolidinophenyl)-2-(3,4-diethoxyphenyl)ethenyl]-4,5,6,7-tetrachlorophthalide.

29. A recording material comprising a material containing a divinyl compound represented by the formula (I) as a chromogenic agent:

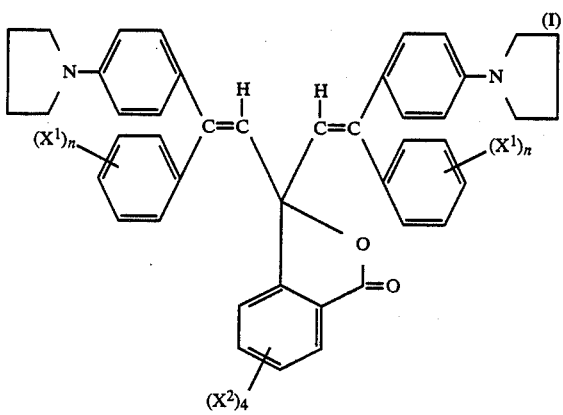

wherein $X^1$ is selected from the group consisting of an alkyl group of not more than six carbon atoms, an alkoxy group of not more than eight carbon atoms, an alkoxy-alkoxy group of not more than six carbon atoms in total, a phenoxy group, a cycloalkoxy group of not more than eight carbon atoms, a haloalkoxy group of not more than eight carbon atoms, an alkenyloxy group of not more than eight carbon atoms, a benzyloxy group and a halogen atom; $X^2$ represents a halogen atom; and n represents an integer of 0, 2 or 3, wherein $X^1$ of $(X^1)_n$ can be the same or different when n is not less than 2 and $X^2$ of $(X^2)_4$ can be the same or different.

30. A recording material according to claim 29, wherein $X^1$ is selected from the group consisting of an alkyl group of not more than 6 carbon atoms, an alkoxy group of not more than 6 carbon atoms, a cyclohexyloxy, a cyclopentyloxy group, a benzyloxy group, an allyloxy group, an alkoxyalkoxy group of not more than 6 carbon atoms in total, a phenoxy group, a phenoxy group substituted by an alkyl group of not more than eight carbon atoms or an alkoxy group of not more than eight carbon atoms and a halogen atom; $(X^2)_4$ represents four chlorine atoms, four bromine atoms, one chlorine atom and three bromine atoms or two chlorine atoms and two bromine atoms; and n is 0, 1 or 2.

31. A recording material according to claim 29, wherein n is 1.

32. A recording material according to claim 29, wherein $X^1$ is an alkoxy group of not more than four carbon atoms in a para-position and n is 1.

33. A recording material according to claim 29, wherein said divinyl compound is 3,3-bis[2-(p-pyrrolidinophenyl)-2-(p-methoxyphenyl)ethenyl]-4,5,6,7-tetrachloro-phthalide.

34. A recording material according to claim 29, wherein said divinyl compound is 3,3-bis[2-(p-pyrrolidinophenyl)-2-(p-ethoxyphenyl)ethenyl]-4,5,6,7-tetrachloro-phthalide.

35. A recording material according to claim 29, wherein said divinyl compound is 3,3-bis[2-(p-pyrrolidinophenyl)-2-(p-propoxyphenyl)ethenyl]-4,5,6,7-tetrachloro-phthalide.

36. A recording material according to claim 29, wherein said divinyl compound is 3,3-bis[2-(p-pyrrolidinophenyl)-2-(p-isopropoxyphenyl)ethenyl]-4,5,6,7-tetrachloro-phthalide.

37. A recording material according to claim 29, wherein said divinyl compound is 3,3-bis[2-(p-pyrrolidinophenyl)-2-(p-butoxyphenyl)ethenyl]-4,5,6,7-tetrachlorophthalide.

38. A recording material according to claim 29, wherein said divinyl compound is 3,3-bis[2-(p-pyrrolidinophenyl)-2-(p-isobutoxyphenyl)ethenyl]-4,5,6,7-tetrachlorophthalide.

39. A recording material according to claim 29, wherein said divinyl compound is 3,3-bis[2-(p-pyrrolidinophenyl)-2-(p-sec-butoxyphenyl)ethenyl]-4,5,6,7-tetrachlorophthalide.

40. A recording material according to claim 29, wherein said divinyl compound is 3,3-bis[2-(p-pyrrolidinophenyl)-2-(p-tert-butoxyphenyl)ethenyl]-4,5,6,7-tetrachlorophthalide.

41. A recording material according to claim 29, wherein said divinyl compound is 3,3-bis[2-(p-pyrrolidino-phenyl)-2-(m-methyl-p-methoxyphenyl)ethenyl]-4,5,6,7-tetrachlorophthalide.

42. A recording material according to claim 29, wherein said divinyl compound is 3,3-bis[2-(p-pyrrolidinophenyl)-2-(3,4-dimethoxyphenyl)ethenyl]-4,5,6,7-tetrachlorophthalide.

43. A recording material according to claim 29, wherein said divinyl compound is 3,3-bis[2-(p-pyrrolidinophenyl)-2-phenylethenyl]-4,5,6,7-tetrachlorophthalide.

44. A recording material according to claim 29, wherein said divinyl compound is 3,3-bis[2-(p-pyrrolidinophenyl)-2-(p-methylphenyl)ethenyl]-4,5,6,7-tetrachlorophthalide.

45. A recording material according to claim 29, wherein said divinyl compound is 3,3-bis[2-(p-pyrrolidinophenyl)-2-(p-methoxyphenyl)ethenyl]-4,5,6,7-tetrabromophthalide.

46. A recording material according to claim 29, wherein said divinyl compound is 3,3-bis[2-(p-pyrrolidinophenyl)-2-(pentyloxyphenyl)ethenyl]-4,5,6,7-tetrachlorophthalide.

47. A recording material according to claim 29, wherein said divinyl compound is 3,3-bis[2-(p-pyrrolidinophenyl)-2-(p-isopentyloxyphenyl)ethenyl]-4,5,6,7-tetrachlorophthalide.

48. A recording material according to claim 29, wherein said divinyl compound is 3,3-bis[2-(p-pyrrolidinophenyl)-2-(p-chlorophenyl)ethenyl]-4,5,6,7-tetrachlorophthalide.

49. A recording material according to claim 29, wherein said divinyl compound is 3,3-bis[2-(p-pyrrolidino-phenyl)-2-(p-ethoxyphenyl)ethenyl]-4,5,6,7-tetrabromophthalide.

50. A recording material according to claim 29, wherein said divinyl compound is 3,3-bis[2-(p-pyrrolidinophenyl)-2-(m-methoxy-p-ethoxyphenyl)ethenyl]-4,5,6,7-tetrachlorophthalide.

51. A recording material according to claim 29, wherein said divinyl compound is 3,3-bis[2-(p-pyrrolidinophenyl)-2-(m-methyl-p-ethoxyphenyl)ethenyl]-4,5,6,7-tetrachlorophthalide.

52. A recording material according to claim 29, wherein said divinyl compound is 3,3-bis2-(p-pyrrolidinophenyl)-2-(p-methoxyphenyl)ethenyl]-5,6-dichloro-4,7-dibromophthalide.

53. A recording material according to claim 29, wherein said divinyl compound is 3,3-bis{2-(p-pyrrolidinophenyl)-2-[p-(p-methoxyphenoxy)phenyl]ethenyl}-4,5,6,7-tetrachlorophthalide.

54. A recording material according to claim 29, wherein said divinyl compound is 3,3-bis[2-(p-pyrrolidinophenyl)-2-(m-methyl-p-n-propoxyphenyl)ethenyl]-4,5,6,7-tetrachlorophthalide.

55. A recording material according to claim 29, wherein said divinyl compound is 3,3-bis[2-(p-pyrrolidinophenyl)-2-(m-methyl-p-iso-propoxyphenyl)ethenyl]-4,5,6,7-tetrachlorophthalide.

56. A recording material according to claim 29, wherein said divinyl compound is 3,3-bis[2-(p-pyrrolidinophenyl)-2-(3,4-diethoxyphenyl)ethenyl]-4,5,6,7-tetrachlorophthalide.

* * * * *